United States Patent [19]
Isayama et al.

[11] Patent Number: 5,925,786
[45] Date of Patent: Jul. 20, 1999

[54] PROCESS FOR PRODUCING AROMATIC DICARBOXYLIC ACID

[75] Inventors: Shigeru Isayama, Ohtake; Etsuro Okamoto, Kuga-Gun; Toshiyuki Sakata; Hiroshi Suzuki, both of Ohtake; Hideaki Iwata, Chiba, all of Japan

[73] Assignee: Mitsui Chemicals, Inc., Tokyo, Japan

[21] Appl. No.: 09/101,136

[22] PCT Filed: Oct. 28, 1997

[86] PCT No.: PCT/JP97/03908

§ 371 Date: Jun. 30, 1998

§ 102(e) Date: Jun. 30, 1998

[87] PCT Pub. No.: WO98/18750

PCT Pub. Date: May 7, 1998

[30] Foreign Application Priority Data

Oct. 30, 1996 [JP] Japan ................................. 8-287957

[51] Int. Cl.$^6$ .................................................. C07C 51/16
[52] U.S. Cl. ........................................... 562/412; 562/414
[58] Field of Search ..................................... 562/412, 414

[56] References Cited

U.S. PATENT DOCUMENTS 5,093,001  3/1992  Ueda .
5,583,254  12/1996  Turner et al. .
5,698,734  12/1997  Turner et al. .

FOREIGN PATENT DOCUMENTS 59-115451  8/1984  Japan .
6-65143   3/1994  Japan .
7-155643  6/1996  Japan .
8-176064  7/1996  Japan .
WO9324440A1  12/1993  WIPO .

*Primary Examiner*—Samuel Barts
*Attorney, Agent, or Firm*—Birch, Stewart, Kolasch & Birch, LLP

[57] ABSTRACT

A process for producing an aromatic dicarboxylic acid by simple operations using a simple apparatus is disclosed, which enables to effect separation and washing of the product crystals efficiently without suffering from clogging of the apparatus, while permitting recovery of the reaction solvent and catalyst with permission of an efficient replacement of the solvent. According to the present invention, an aromatic dicarboxylic acid is produced by effecting, in the oxidation reactor 1, a liquid phase oxidation of an aromatic compound having substituent groups of alkyl(s) or partly oxidized alkyl(s) in a reaction solvent containing a catalyst with a molecular oxygen-containing gas, wherein the slurry containing the crystals of the aromatic dicarboxylic acid from a slurry receiver 4 or from a purification reactor 7 is introduced into a centrifuge 5a or 5b provided in its solid matter delivery zone with a filtering region to subject it to a centrifugation in order to separate it into the crystals and a separated liquid, whereupon the so-separated crystals are filtered in the filtering region on their way of travelling across the solid matter delivery zone while contacting them with a washing liquid and discharging the spent washing liquid from the filtering region.

5 Claims, 2 Drawing Sheets

PROCESS FOR PRODUCING AROMATIC DICARBOXYLIC ACID

This application is the national phase under 35 U.S.C. §371 of prior PCT International Application No., PCT/JP97/03908, which has an International filing date of Oct. 28, 1997, which designated the United States of America, the entire contents of which are hereby incorporated by reference.

FIELD OF THE TECHNIQUE

The present invention relates to a process for producing an aromatic dicarboxylic acid, such as terephthalic acid or naphthalene dicarboxylic acid, and specifically, to a process for the production of an aromatic dicarboxylic acid in which the product crystals formed thereby are separated efficiently.

BACKGROUND OF THE TECHNIQUE

In a process for producing an aromatic dicarboxylic acid, such as terephthalic acid or naphthalene dicarboxylic acid, using, as the raw material, an aromatic compound having substituent groups of alkyl or partially oxidized alkyl, such as paraxylene or a dialkyl naphthalene, by subjecting it to a liquid phase oxidation with molecular oxygen, the thereby produced aromatic dicarboxylic acid will deposit out as crystals to form a slurry. Since the so-formed slurry contains the reaction catalyst, reaction solvent and so on, in addition to the crystals of the aromatic dicarboxylic acid, it is necessary to separate them to recover the crystals.

Explaining now the process by an example of production of terephthalic acid by a liquid phase oxidation of paradialkylbenzene, the thereby produced terephthalic acid deposits out of the mother liquor as crystals to form a slurry containing the terephthalic acid crystals. By recovering the crystals from, such a slurry, a crude terephthalic acid product is obtained. By dissolving the so-obtained crude terephthalic acid, subjecting the resulting solution to purification procedures, such as oxidation treatment, reduction treatment and so on, and then causing terephthalic acid to be deposited out, a crystal-containing slurry is obtained. By recovering the crystals from this slurry, purified terephthalic acid is obtained.

For recovering the crystals from the slurry, it has heretofore been practised in both cases, to subject the slurry to a solid/liquid separation using a filter or a centrifuge, followed by reslurrying the so-filtered crystals in a washing liquid and subjecting the slurry to a solid/liquid separation using a filter or a centrifuge and, if necessary, repeating such procedures many times. In such a technique, however, there is a problem that the process steps are complicate and the apparatus therefor becomes larger.

Therefore, a technique has been adopted as an alternative therefor, in which a series of process steps of pressure/suction filtration, washing and pressure/suction filtration are performed all at once on a rotary filter (Japanese Patent Kokai Hei-1-299618 A, corresponding to U.S. Pat. No. 5,093,001). This technique carries out a pressure/suction filtration, washing of the filtered cake, a pressure/suction filtration of the reslurry and removal or exfoliation of the filtered cake successively in order while rotating a cylindrical filter medium (filter cloth). If a rotary vacuum filter is employed for the rotary filter to effect a sucking filtration of wet cake in this technique, deposition of crystals would occur due to the condition of negative pressure on the filtrate side, resulting in a clogging of the filter. Therefore, the filtration and washing of the wet cake are realized in this technique by pressurizing the wet cake, in order to prevent any crystal deposition to occur.

In rotary filters however, a larger unit for gas circulation is necessary not only for sucking filtration but also for pressure filtration. Moreover, an efficient replacement of the reaction solvent may difficultly be achieved, since the circulation gas will pass through the wet cake after the gas has received the vaporized acetic acid, whereby acetic acid will remain in the crystals. Moreover, it is necessary to install a means for interrupting pressure in the passage for delivering the crystals, since the apparatus is kept pressurized in case the wet cake is subjected to a pressure filtration in a rotary filter.

The object of the present invention is to provide a process for producing an aromatic dicarboxylic acid which permits an efficient separation and washing of the product crystals by simple procedures using a simple apparatus without suffering from clogging of the filter and which can afford to recover the reaction solvent and the catalyst and to perform an efficient reaction solvent replacement as well.

DISCLOSURE OF THE INVENTION

The process for producing an aromatic dicarboxylic acid, according to the present invention, by liquid phase oxidation of an aromatic compound having substituent groups of alkyl(s) or partly oxidized alkyl(s) with a molecular oxygen-containing gas in a reaction solvent containing a catalyst, comprises introducing a slurry containing crystals of the aromatic dicarboxylic acid formed by the reaction into a centrifuge provided in the solid matter delivery zone with a filtering region to effect centrifugation to separate the slurry into crystals and a filtrate, subjecting the so-separated crystals to filtration in the filtering region on their way of travelling across the solid matter delivery zone, while contacting them with a washing liquid and exhausting the spent washing liquid out from the filtering region by making use of the centrifugal force to effect washing of the crystals.

It is preferable to apply the process according to the present invention for producing terephthalic acid or naphthalene dicarboxylic acid.

As the starting material to be oxidized for producing an aromatic dicarboxylic acid in the process according to the present invention, an aromatic compound having substituent groups of alkyl(s) or partly oxidized alkyl(s) (denoted hereinafter sometimes simply as the starting material to be oxidized) may be used. Such an aromatic compound may either be monocyclic or polycyclic. As the substituent alkyl group, there may be exemplified alkyl groups having 1–4 carbon atoms, such as methyl, ethyl, n-propyl and isopropyl. For the partly oxidized alkyl group, there may be enumerated, for example, aldehydo, acyl, carboxyl and hydroxyalkyl.

Concrete examples of the aromatic compound having substituent groups of alkyl(s), there may be exemplified dialkylbenzenes having two alkyl groups of 1–4 carbon atoms, such as m-diisopropylbenzene, p-diisopropylbenzene, m-cymene, p-cymene, m-xylene and p-xylene; dialkylnaphthalenes having two alkyl groups of 1–4 carbon atoms, such as dimethylnaphthalenes, diethylnaphthalenes and diisopropylnaphthalenes; and dialkylbiphenyls having two alkyl groups of 1–4 carbon atoms, such as dimethylbiphenyls and the like.

The aromatic compound having substituent groups of partly oxidized alkyl(s) are those in which the alkyl groups of the afore-mentioned compounds are partly oxidized into, for example, aldehydo, acyl, carboxyl and hydroxyalkyl, as mentioned above. Concretely, there may be enumerated, for example, 3-methylbenzaldehyde, 4-methylbenzaldehyde, m-toluic acid, p-toluic acid, 3-formylbenzoic acid, 4-formylbenzoic acid and formylnaphthalenecarboxylic acid.

These starting materials to be oxidized may be used either solely or in a mixture of two or more of them.

In the process according to the present invention, a heavy metal compound and a bromine compound are used as the catalyst, which may be exemplified as follows: Thus, as the heavy metal in the heavy metal compound, there may be enumerated, for example, cobalt, manganese, nickel, chromium, zirconium, copper, lead, hafnium or cerium. They may be used either alone or in a combination of two or more of them, wherein a combination of cobalt and manganese is especially preferable.

For the compounds of such heavy metals, there may be enumerated, for example, acetate, nitrate, acetylacetonato salt, naphthenate, stearate and bromide, wherein acetate is particularly preferable.

As the bromide, there may be enumerated, for example, inorganic bromine compounds including molecular bromine, hydrogen bromide, sodium bromide, potassium bromide, cobalt bromide and manganese bromide; and organic bromine compounds, such as methyl bromide, methylene bromide, bromoform, benzyl bromide, bromomethyltoluene, dibromoethane, tribromoethane and tetrabromoethane.

These bromine compounds may also be used either alone or in a mixture of two or more of them.

According to the present invention, the catalyst constituted of a combination of the heavy metal compound and the bromine compound as given above may favorably have a mole ratio in the range of 0.05–10 moles, preferably 0.1–2 moles of bromine per one mole of the heavy metal. Such a catalyst may be used usually at a concentration of the heavy metal in the reaction solvent in the range of 10–10,000 ppm, preferably 100–5,000 ppm.

In the process according to the present invention, the aromatic compound served as the starting material to be oxidized is subjected to a liquid phase oxidation in a reaction solvent containing a lower aliphatic carboxylic acid with a molecular oxygen-containing gas in the presence of the above-mentioned catalyst.

As the molecular oxygen-containing gas, there may be enumerated, for example, pure oxygen gas or atmospheric air, while air is employed preferably in the practice. The molecular oxygen-containing gas is supplied to the reaction system in a somewhat excessive amount as compared with that required for oxidizing the aromatic compound served for the starting material to be oxidized into the corresponding aromatic dicarboxylic acid. When air is used as the molecular oxygen-containing gas, it is supplied to the reaction system favorably at a rate of 2–20N m$^3$, preferably 2.5–15N m$^3$ per one kilogram of the aromatic compound served for the starting material to be oxidized.

As concrete ones of the lower aliphatic carboxylic acid to be used as the reaction solvent, for example, acetic acid, propionic acid and butyric acid may be enumerated. The lower aliphatic carboxylic acid may be used alone as the reaction solvent or may be used in a state of a mixture with water as the reaction solvent. As the reaction solvent, there may be enumerated concretely, for example, acetic acid, propionic acid, butyric acid and mixtures of them as well as a mixture of such an aliphatic carboxylic acid with water.

Among them, preference is given to a mixture of acetic acid with water, wherein a mixture of 1–20 parts by weight, preferably 5–15 parts by weight of water per 100 parts by weight of acetic acid is especially preferred.

The reaction solvent may be used in an amount in the range of 0.5–70 parts by weight, preferably 2–50 parts by weight, more preferably 2–6 parts by weight of the reaction solvent per one part by weight of the aromatic compound served for the starting material to be oxidized, namely at a solvent weight ratio in the range of 0.5–70, preferably 2–50 and more preferably 2–6.

The reaction duration in the process according to the present invention is adjusted within the range of 180 minutes–4 minutes, preferably 120 minutes–6 minutes, more preferably 90 minutes–6 minutes. Here, when the oxidation is carried out in continuous mode, the reaction duration is the residence time in the reactor.

A part of the aromatic dicarboxylic acid produced by the oxidation reaction will deposit as crystals out of the reaction solvent to form a slurry, while the other part is left dissolved therein. In the process according to the present invention, separation of the crystals is carried out both from the reaction product slurry and from the slurry formed during the purification step. By separating the crystals from the slurry formed during the reaction step, a crude aromatic dicarboxylic acid is obtained. When the product is brought to practical use in the state of crude aromatic dicarboxylic acid, a lower aliphatic carboxylic acid, such as acetic acid, may be used as the washing liquid.

The crude aromatic dicarboxylic acid may also be subjected to a purification step including combination of unit operations, such as hydrogenation, crystallization and esterification into methyl ester, to obtain purified aromatic dicarboxylic acid. As concrete examples of the solvent to be used in the purification step, water and lower aliphatic alcohols may be enumerated. When the reaction solvent in the crude product slurry formed in the oxidation reaction is replaced by the solvent to be used in the purification step, the solvent used in the purification step can be used as the washing liquid.

For the centrifuge for separating the crystals, every voluntary one, such as the decanter type and basket type, may be employed, wherein a decanter type one is preferred. In each case, a centrifuge which is constructed so that the centrifugation is effected in a separation zone and the separated crystals are exhausted via a solid matter delivery zone in which the filtration and washing of the crystals are carried out can be used.

As the centrifuge, such one may be used, which comprises a separation zone for separating the slurry into the solid matter and the separated liquor, a solid matter delivery zone for effecting discharge of the separated solid matter, a liquor extracting region for extracting the separated liquor, a slurry supply region for guiding the slurry to the separation zone, a filtering region disposed in the solid matter delivery zone, a washing liquid supply region for supplying the washing liquid to the crystals which has passed the filtering region and a spent washing liquid withdrawal region for withdrawing the spent washing liquid which has passed the filtering region. It is preferable here, that the washing liquid supply region is arranged in a plurality of stages along the region in the direction towards the discharge of the crystals, wherein the spent washing liquid withdrawal part of a subsequent stage is connected to the washing liquid supply part of the preceding stage so as to effect the washing of the crystals in a counter flow sense. Here, "counter flow sense" is to be understood so that it is enough that the direction of the washing liquid as a whole is reverse to the travelling direction of the crystals as a whole and, thus, the flow direction of the washing liquid may at a certain local part intersect the crystal layer in right angle or even lie in a parallel flow therewith.

In the separation and recovery of the crystals by means of the centrifuge, the slurry formed in the oxidation reaction step or the slurry formed in the purification step is supplied to the slurry supply region, in which the slurry is separated in the separation zone into the solid matter and the separated liquor by the centrifugal force due to a high speed rotation thereof. On the side of the separated liquor, the lower aliphatic carboxylic acid (acetic acid) as the reaction solvent and, dissolved therein, the catalyst, unreacted raw material, by-products and the aromatic dicarboxylic acid left undeposited are transferred. On the side of the solid matter, a part of the mother liquor is transferred together with the crystals of aromatic dicarboxylic acid.

The separated liquor is extracted from the liquor extracting region and the solid matter is discharged out via the solid matter delivery zone. Here, the mother liquor retained in the solid matter is separated by the centrifugal force in the filtering region. At the same time, the washing liquid is supplied thereto via the washing liquid supply region in order to bring it into contact with the crystals and then to discharge it out of the filtering region to effect the washing of the crystals. Here, it is possible to increase the washing effect by supplying the washing liquid to the filtering region in a plurality of washing liquid supply stages to repeat the washing procedure on many stages. A further increase in the washing efficiency can be attained when the spent washing liquid of a subsequent washing stage is used as the washing liquid in the preceding stage to effect the washing in a counter flow sense.

By the washing, a crystal product having no adsorbed mother liquor is obtained. When a washing liquid consisting of the same solvent as the mother liquor is employed, the spent washing liquid can be returned as such to the oxidation reactor and, in addition, the lower aliphatic carboxylic acid can be separated easily from the crystals by heating it. When a washing liquid consisting of a solvent different from that in the mother liquor is employed, namely, for example, when water is used as the washing liquid for the slurry formed in the oxidation reaction, replacement of the solvent can be reached, wherein the recovered crystals can be transferred as such to the purification step where it is dissolved in water and is subjected to a purifying treatment, such as oxidation, reduction and so on. Here, it is possible to return the spent washing liquid to the reaction step after it has been supplemented with, for example, acetic acid.

The oxidation reaction step may be performed in an oxidation reactor equipped at the upper part thereof with a distillation column wherein the condensate of the vapour coming from the distillation column is used as the washing liquid, whereby a closed system for carrying out the process can be established.

Since the separation of the liquid phase and the solid matter by the centrifuge in the separation zone, the removal of the mother liquor in the filtering region and the withdrawal of the spent washing liquid are all performed by making use of the centrifugal force, no phenomenon of deposition of crystals due to lowering of pressure and temperature can occur. For this reason, no clogging in the filtering region does occur, so that separation of the crystals from the mother liquor and recovery of the solvent and catalyst are attained efficiently.

As described above, the process for producing an aromatic dicarboxylic acid according to the present invention can afford to realize efficient separation and washing of the crystals using a simple apparatus with simple procedures without suffering from clogging of the apparatus and, in addition, to attain recovery of the solvent and catalyst together with permission of efficient replacement of the solvent.

By effecting supply of the washing liquid in a plurality of stages, repeated washing of the crystals can be realized, whereby the washing effect is increased.

Moreover, the washing can be realized in a counter flow sense by utilizing the spent washing liquid of a subsequent stage as the washing liquid in the preceding stage, whereby a further increase in the washing effect can be attained, so that the spent washing liquid has a more higher concentration of the washed out solvent, catalyst and so on, to thereby enable to recover them with smaller amount of the spent washing liquid to recycle the recovered substances back to the reaction to reuse them.

THE BEST MODE FOR EMBODYING THE INVENTION

Below, the present invention is described by way of an embodiment with reference to the drawings.

Figure 1:
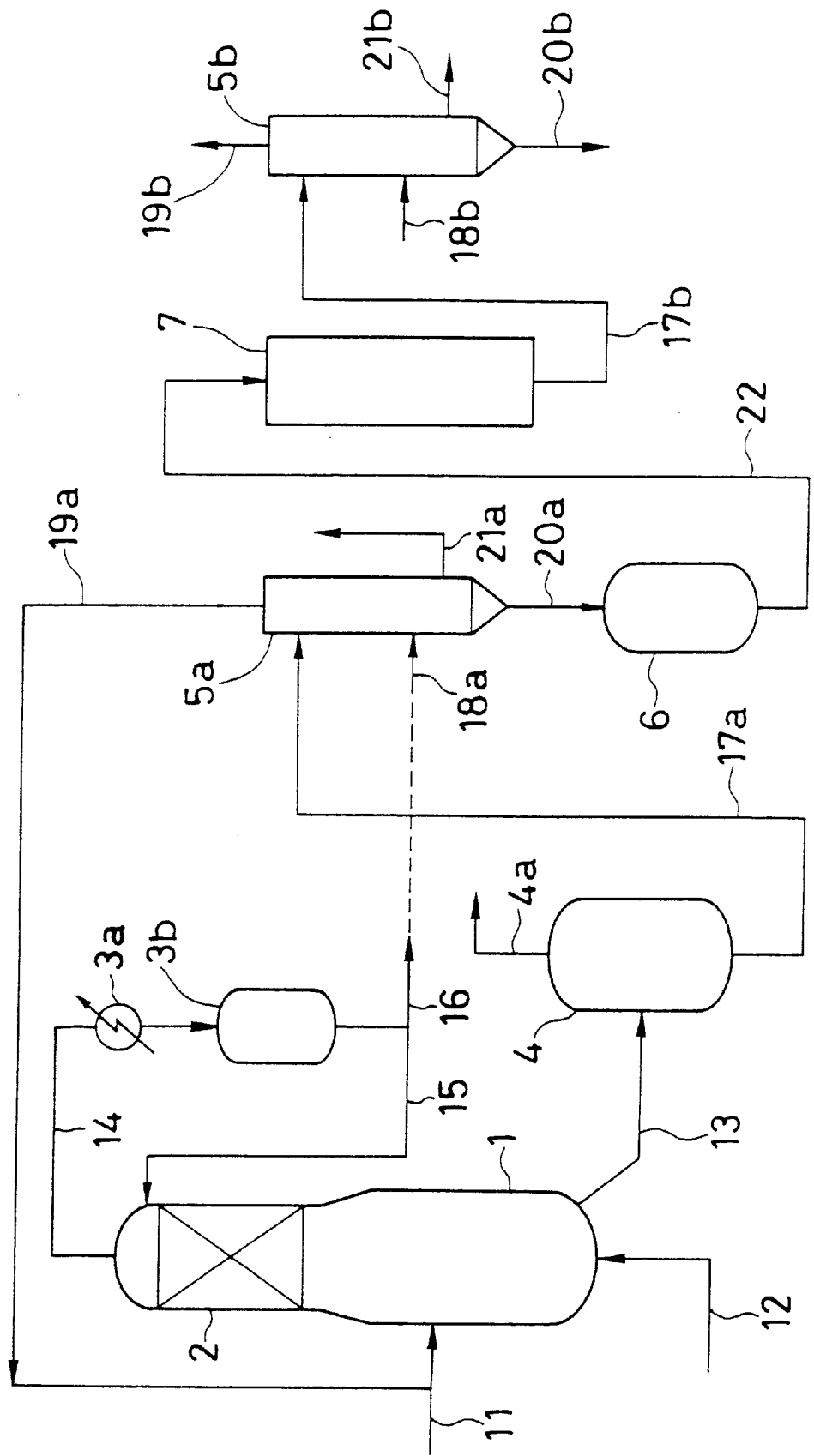
FIG. 1 is a flow sheet explaining the process for producing terephthalic acid as an embodiment.

FIG. 1 shows a flow sheet for an embodiment of production of terephthalic acid.

In FIG. 1, 1 denotes the oxidation reactor, 2 is the distillation column, 3a is the condenser, 3b is the condensate drum, 4 is the slurry receiver, 5a is a first centrifuge, 6 is the dissolving tank, 7 is the purification reactor and 5b is a second centrifuge.

For producing terephthalic acid, there are supplied to the oxidation reactor 1 paraxylene as the starting material, acetic acid as the reaction solvent, a catalyst containing cobalt, manganese and bromine from a starting material supply line 11 and a molecular oxygen-containing gas from an oxygen supply line 12 to oxidize paraxylene to form terephthalic acid. A part of the so-formed terephthalic acid will deposit out of the solvent as crystals to form a slurry. The so-formed slurry is taken out from a slurry discharge line 13 in a state containing the solvent and catalyst to the slurry receiver 4. Here, the slurry is flashed whereby the pressure and temperature thereof are decreased and a further deposition of the crystals occurs. The vapor after the flashing is discharged out of the system via a line 4a.

The oxidation exhaust gas from the oxidation reactor 1 enters the distillation column 2 together with the water steam vaporized by the heat of reaction or so on. Here, distillation takes place by making use of the heat of the steam and of the oxidation exhaust gas guided from the oxidation reactor 1, whereby the starting material, i.e. paraxylene, and the solvent, i.e. acetic acid, are returned back to the oxidation reactor 1 and the vapor containing some acetic acid is fowarded to the condenser 3a via a line 14 and is condensed there and stored in the condensate drum 3b, from which a part of the condensate is returned to the distillation column 2 via a line 15 and the remainder is discharged out via a line 16.

The centrifuges 5a and 5b perform centrifugation of the slurry supplied from the slurry receiver 4 or from the refinery reactor 7 via a slurry supply line 17a or 17b and the separated terephthalic acid crystals are washed by the washing liquid supplied thereto from a washing liquid supply line 18a or 18b, whereupon the separated liquor is extracted via a liquor extracting line 19a or 19b, the separated terephthalic acid crystals are discharged as a wet cake via a wet cake discharge line 20a or 20b and the spent washing liquid is withdrawn via a spent washing liquid withdrawal line 21a or 21b. As the washing liquid, the reaction solvent (acetic acid) and water may be used and the condensate water discharged via the line 16 as well.

The wet cake discharged via the wet cake discharge line 20a is a crude product of terephthalic acid which can be served as such for the final product, but can be processed by forwarding it to the purification reactor 7 via a line 22 after having been dissolved in water or so on, where it is subjected to purification reaction including oxidation and/or reduction to cause a high purity terephthalic acid to deposit out. The slurry formed in this manner is subjected to a centrifugation on the centrifuge 5b and the separated crystals are washed to thereby obtain crystals of high purity terephthalic acid which is taken out via the wet cake discharge line 20b.

The separated liquor extracted via the separated liquor extracting line 19a may be recycled as such to the oxidation reactor 1 in order to subject it to the oxidation reaction. The spent washing liquid withdrawn via the spent washing liquid withdrawal line 21a can be utilized as such for the liquid for preparing the starting material solution in case acetic acid is used as the washing liquid, since the spent washing liquid also contains the solvent, catalyst and so on. Even if water is used as the washing liquid, the spent washing liquid can be used as the liquid for preparing the starting material solution so long as the concentration of the washed out solvent, catalyst and so on in the spent washing liquid has been increased by the manner of washing in counter flow sense.

Figure 2:
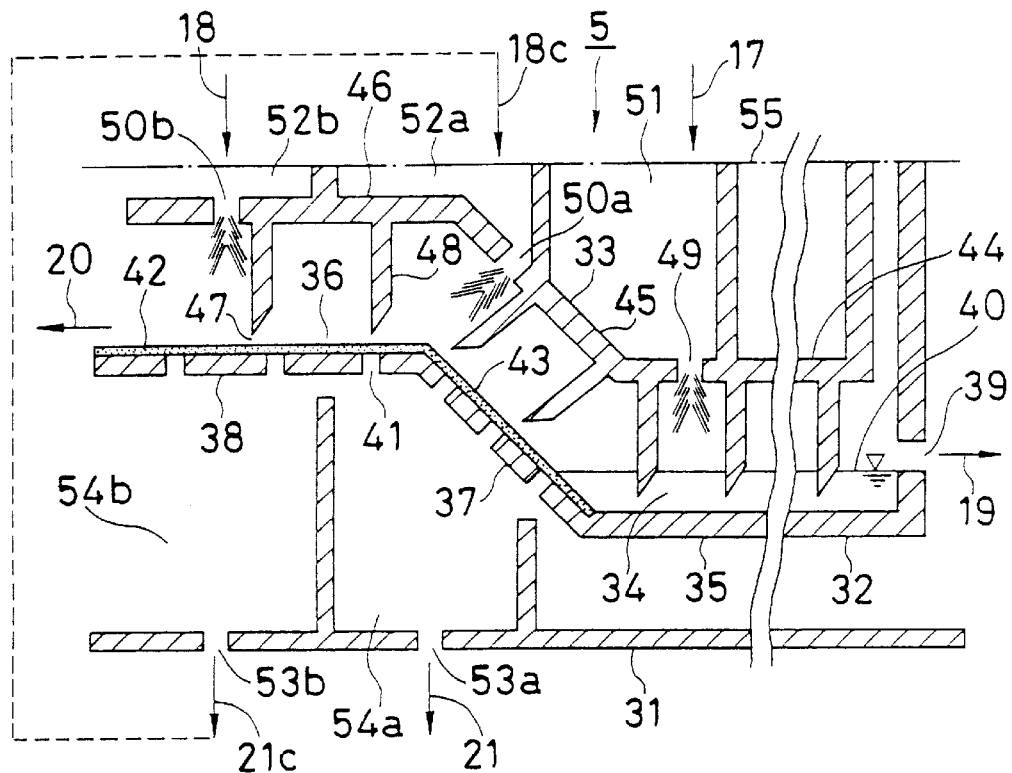
FIG. 2 is a partial sectional view of an embodiment of the centrifuge.
Figure 3:
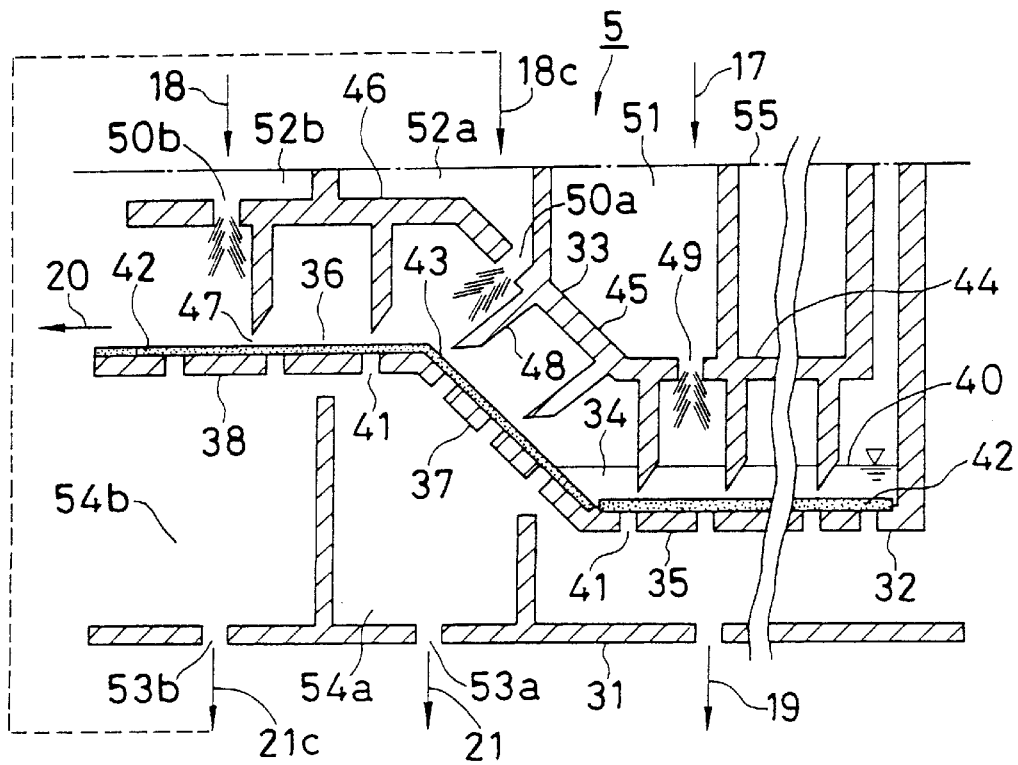
FIG. 3 is a partial sectional view of another embodiment of the centrifuge.

FIGS. 2 and 3 illustrate each a different embodiment of centrifuge in a partial sectional view laid as a horizontal machine for easy understanding.

In FIG. 2, the centrifuge 5 is a decanter type one in which a rotary separator cylinder 32 provided therein with a screw conveyer 33 relatively rotatably is disposed within the casing 31 so as to permit high speed rotation.

The rotary separator cylinder 32 has a large diameter part 35 of a cylindrical form to be served as the separation zone 34, a slanting part 37 of a conical form to be served as the solid matter delivery zone 36 and a small diameter part 38 in a form of small diameter cylinder. The large diameter part 35 is arranged so as to build up a liquid level 40 by an overflow exit 39 connected to the separated liquor extracting line 19. On the slanting part 37 and on the small diameter part 38 are disposed many liquid exits 41, on the insides of which are arranged each a porous filter medium 42 to build up the filtering region 43.

The screw conveyer 33 is provided with a large diameter part 44, a slanting part 45 and a small diameter part 46 so as to extend nearly parallel to the rotary separator cylinder 32 and has a screw blade 48 which extends outwards so as to maintain a small gap 47 between the outer extremity of the screw blade and the inside face of the rotary separator cylinder 32. The large diameter part 44, the slanting part 45 and the small diameter part 46 of the screw conveyer 33 are provided each with a slurry supply inlet 49 or a washing liquid supply inlet 50a or 50b, respectively, so as to build up internally a slurry supply region 51 or a washing liquid supply region 52a or 52b, respectively.

In the casing 31, spent washing liquid withdrawal exits 53a and 53b for the preceding and the subsequent stages are disposed in opposition to the slanting part 37 and to the small diameter part 38 of the rotary separator cylinder 32, respectively, wherein the inside thereof are arranged spent washing liquid withdrawal regions 54a and 54b. The above construction is in a rotational symmetry with respect to the center line 55. A spent washing liquid withdrawal line 21 (corresponding to the lines 21a and 21b of FIG. 1) communicates to the spent washing liquid withdrawal exit 53a and a spent washing liquid withdrawal line 21c communicates to the spent washing liquid withdrawal exit 53b and is connected to the washing liquid supply line 18c of the preceding stage.

For separation and recovery of the crystals by means of the centrifuge 5, the slurry obtained in the oxidation reaction step or the slurry obtained in the purification step is supplied to the slurry supply region 51 via the slurry supply line 17 and is guided into the large diameter part 35 of the rotary separator cylinder 32, in order to separate it into the separated liquor and the solid matter by centrifugation in the separation zone 34 rotating at a high speed. To the side of the separated liquor, acetic acid as the solvent and, dissolved therein, the catalyst, unreacted starting material, by-products and the undeposited terephthalic acid are transferred. To the side of the solid matter, the crystals of terephthalic acid and a part of the mother liquor are transferred.

The separated liquor is extracted via the separated liquor extracting line 19 and the solid matter is discharged via the wet cake discharge line 20 through the solid matter delivery zone 36 of the slanting part 37 and the small diameter part 35. At this occasion, the mother liquor is separated from the solid matter by the centrifugal force in the filtering region 43. At the same time, the washing liquid supplied via the washing liquid supply regions 52a and 52b is sprayed onto the crystal layer to contact with the crystals of terephthalic acid before being discharged out through the filtering region 43 to perform washing of the crystals. Here, the washing effect can be increased by repeating the washing operation in a plurality of washing stages by supplying the washing liquid via a plurality of washing liquid supply regions 52a and 52b. By supplying the spent washing liquid of a subsequent washing stage via the spent washing liquid withdrawal line 21c to the washing liquid supply line 18c of the preceding washing stage to use there as the washing liquid, washing can be realized in a counter flow sense, whereby the washing effect can further be increased.

In the embodiment shown in FIG. 3, the filter medium 42 is disposed over the inside face of the large diameter part 35 so that the solvent is discharged out through the filter medium 42 by a centrifugal force which permits to maintain a liquid level at about 40, whereby the amount of the crystals lost by flowing out together with the separated liquor can be reduced.

In the construction given above, either one of the washing liquid supply inlets 50a and 50b and either one of washing liquid supply regions 52a and 52b can occasionally be dispensed with. In this case, the filter medium 42 can be arranged either in the slanting part 37 or in the small diameter part 38.

By the washing as described above, a crystal product having no adsorbed mother liquor is obtained. When a washing liquid consisting of the solvent same as that in the mother liquor is used here, it is possible to return the spent washing liquid as such to the oxidation reactor 1 and it is also possible to separate the lower aliphatic carboxylic acid easily from the crystals by heating. When a washing liquid different from the solvent in the mother liquor is employed, namely, when, for example, water is used as the washing liquid for the slurry obtained in the reaction step, exchange of the solvent can be realized, wherein the crystals recovered can be transferred as such to the purification step to subject them to the purification procedures, such as oxidation, reduction and so on, after having been dissolved in water. In this case, the spent washing liquid can be returned to the reaction step after having been replenished with, such as, acetic acid and so on.

Since the oxidation reactor 1 is provided at its top with the distillation column 2 and the vapor exhausted from the distillation column 2 is condensed in the condenser 3a, as shown in FIG. 1, a closed system can be built up, when the condensate withdrawn from the condenser 3a is used as the washing liquid for the centrifuge 5.

Because of that the separation of the liquid phase from the solid matter in the separation zone 34, the removal of the mother liquor in the filtering region 43 and the discharge of the spent washing liquid in the centrifuge 5 are all realized by making use of centrifugal force, no deposition of crystals due to a pressure drop or a temperature decrease can occur. Therefore, it is possible to realize separation of the crystals and recovery of the solvent and catalyst efficiently without suffering from clogging of the filtering region 43.

Below, the invention is described by way of Examples.

EXAMPLE 1

A terephthalic acid/acetic acid slurry (120° C., a terephthalic acid content of 40% by weight) obtained from the slurry receiver 4 in the process for producing terephthalic acid as shown in FIG. 1 was supplied to a centrifuge 5 as shown in FIG. 2 at a rate of 2,500 kg/hr and terephthalic acid crystals were recovered from the slurry by centrifugation. In the acetic acid solution in the starting slurry, cobalt acetate served for the oxidation catalyst was contained in an amount of 6 kg/hr calculated as metallic cobalt.

Pure water was supplied as the washing liquid to the washing liquid supply line 18 as shown in FIG. 2 at a rate of 500 kg/hr to effect washing, whereupon the spent washing liquid was withdrawn via the spent washing liquid withdrawal line 21c and was supplied to the washing liquid supply line 18c of the preceding washing stage to realize washing in a counter flow sense. Hereby 995 kg/hr of terephthalic acid, 240 kg/hr of water, 1 kg/hr of acetic acid and 0.008 kg/hr of the catalyst metal were obtained at the wet cake discharge line 20 as a wet cake.

EXAMPLE 2

When a two-stage washing was carried out similarly in a counter flow sense using 1,000 kg/hr of pure acetic acid as the washing liquid as in Example 1, 995 kg/hr of terephthalic acid, 249 kg/hr of acetic acid and 0.008 kg/hr of the catalyst metal were obtained at the wet cake discharge line 20 as a wet cake.

By forwarding this wet cake to a drying step, 995 kg/hr of terephthalic acid, 1 kg/hr of acetic acid and 0.008 kg/hr of the catalyst metal were obtained as a dry cake.

EXAMPLE 3

A two-stage washing as in Example 2 was carried out wherein, instead of the counter flow washing, 1,025 kg/hr of pure acetic acid were supplied to the washing liquid supply lines 18 and 18c and the corresponding spent washing liquids were withdrawn from the spent washing liquid withdrawal lines 21c and 21, respectively, whereby 995 kg/hr of terephthalic acid, 265 kg/hr of acetic acid and 0.006 kg/hr of the catalyst metal were obtained at the wet cake discharge line 20 as a wet cake.

EXAMPLE 4

A terephthalic acid/water slurry (100° C., a terephthalic acid content of 40% by weight) obtained from the hydrogenation purification step in the purification reactor 7 in a process for producing terephthalic acid was supplied to the centrifuge 5 as shown in FIG. 2 at a rate of 2,500 kg/hr and terephthalic acid crystals were recovered from the slurry by centrifugation. In the starting slurry, 0.8 kg/hr of paratoluic acid as a by-product was contained. Washing was performed by supplying pure water as the washing liquid to the washing liquid supply line 18 at a rate of 500 kg/hr, whereupon the spent washing liquid was withdrawn via the spent washing liquid withdrawal line 21c but was not supplied to the washing liquid supply line 18c. Hereby 995 kg/hr of terephthalic acid, 110 kg/hr of water and 0.10 kg/hr of paratoluic acid were obtained at the wet cake discharge line 20 as a wet cake.

Comparative Example 1

To three conventional centrifuges of decanter type having no filtering region, the terephthalic acid/acetic acid slurry of Example 1 was supplied at a rate of 2,500 kg/hr successively to carry out separation and washing of the crystals. Thus, the slurry was supplied to the first centrifuge to cause centrifugation. Then, the separated crystals were reslurried in the separated liquor of the third centrifuge and the resulting slurry was subjected to centrifugation in the second centrifuge, whereupon the separated crystals were reslurried by mixing therewith 1,000 kg/hr of pure acetic acid and the resulting slurry was subjected to centrifugation in the third centrifuge. There were obtained 995 kg/hr of terephthalic acid, 260 kg/hr of acetic acid and 0.012 kg/hr of the catalyst metal at the crystal discharge exit of the third centrifuge as a wet cake.

Comparative Example 2

The terephthalic acid/water slurry of Example 4 was supplied to a conventional centrifuge of decanter type at a rate of 2,500 kg/hr to effect separation and washing of the crystals. Here, the washing was carried out by spraying pure water onto the wet cake in the solid matter delivery zone at a rate of 500 kg/hr. There were obtained 995 kg/hr of terephthalic acid, 240 kg/hr of water and 0.125 kg/hr of paratoluic acid at the crystal discharge exit of the centrifuge as a wet cake.

Applicability in Industry

By the process according to the present invention, it is possible to carry out separation and washing of the product crystals efficiently using a simple apparatus by simple procedures without suffering from clogging of the apparatus while permitting recovery of the reaction solvent and catalyst with simultaneous attainment of an efficient solvent replacement, so that it can be applied to production of an aromatic dicarboxylic acid, especially terephthalic acid or naphthalene dicarboxylic acid.

We claim:

1. A process for producing an aromatic dicarboxylic acid by liquid phase oxidation of an aromatic compound having substituent groups of alkyl(s) or partly oxidized alkyl(s) with a molecular oxygen-containing gas in a reaction solvent containing a catalyst, comprising introducing a slurry containing crystals of the aromatic dicarboxylic acid formed by the reaction into a centrifuge provided in its solid matter delivery zone with a filtering region to effect centrifugation to separate the slurry into crystals and a filtrate, subjecting the so-separated crystals to filtration in the filtering region on their way of travelling across the solid matter delivery zone, while contacting them with a washing liquid and discharging the spent washing liquid out from the filtering region by making use of the centrifugal force to effect washing of the crystals.

2. A process as claimed in claim 1, wherein the crystals are those of terephthalic acid or naphthalene dicarboxylic acid.

3. A process as claimed in claim 1 or 2, wherein the centrifuge is that of the decanter type.

4. A process as claimed in either one of claims 1 or 2, wherein the supply of the washing liquid is effected on a plurality of stages in order to repeat the washing procedures.

5. A process as claimed in claim 4, wherein the spent washing liquid of a subsequent stage is used in its preceding stage.

* * * * *